United States Patent [19]
Wang et al.

[11] Patent Number: 5,631,425
[45] Date of Patent: May 20, 1997

[54] METHOD FOR IDENTIFYING MOLDING COMPOUND USING AN ACOUSTIC MICROSCOPE

[75] Inventors: Willy C. Wang, San Francisco; Steve K. Sue, Richmond, both of Calif.

[73] Assignee: Integrated Device Technology, Inc., Santa Clara, Calif.

[21] Appl. No.: 612,220

[22] Filed: Mar. 7, 1996

[51] Int. Cl.⁶ .......................... G01N 29/18; G01N 29/20
[52] U.S. Cl. ........................ 73/606; 73/597; 73/599
[58] Field of Search .................... 73/606, 597, 599, 73/602

[56] References Cited

U.S. PATENT DOCUMENTS

| | | | |
|---|---|---|---|
| 4,563,898 | 1/1986 | Kanada et al. | 73/606 |
| 5,212,987 | 5/1993 | Dransfeld et al. | 73/579 |
| 5,224,382 | 7/1993 | Karaki | 73/606 |
| 5,235,271 | 8/1993 | Kira | 324/158 R |
| 5,319,977 | 6/1994 | Quate et al. | 73/606 |
| 5,469,744 | 11/1995 | Patton et al. | 73/644 |
| 5,559,292 | 9/1996 | Hull et al. | 73/597 |

OTHER PUBLICATIONS

T.M. Moore, "SAM Provides Critical IC Inspection", Tech Spotlight, reprinted from the Oct. 1990 issue of *Advanced Materials & Processes*. (3 pages).

(author unknown), "What is an Acoustic Microscope?", [additional information unknown], published prior to Mar. 7, 1996. (6 pages).

J. Siettmann, et al., "Acoustic Evaluation of Electronic Plastic Packages", pp. 309–314, IEEE International Reliability Physics Symposium, (1992).

S.R. Martell, et al., "Nondestructive Evaluation of Microelectronic Components by Acoustic Microscope", SONOSCAN, Inc., Bensenville, IL, published prior to Mar. 7, 1996. (16 pages).

*Primary Examiner*—John E. Chapman
*Attorney, Agent, or Firm*—Isabelle R. McAndrews; Earl A. Bright, II

[57] ABSTRACT

A non-destructive method of identifying a type of molding compound in a sample using an acoustic microscope, particularly, identifying the type of molding compound used in an integrated circuit package by comparing attributes of the tested molding compound with known attributes of standard molding compounds to identify the molding compound being evaluated. The attributes that are compared include voltage, attenuation, peak frequency, average frequency, and the velocity of reflected sound.

15 Claims, 1 Drawing Sheet

METHOD FOR IDENTIFYING MOLDING COMPOUND USING AN ACOUSTIC MICROSCOPE

BACKGROUND OF THE INVENTION

1. Field of the Invention

The present invention relates to the use of acoustic microscopes for non-destructive valuation and, more particularly, to identifying molding compounds using an acoustic microscope.

2. State of the Art

Integrated circuit packages (i.e., chip packages or IC packages) normally comprise integrated circuit devices encapsulated with molding compounds comprised of resin and silica. There are several standard molding compounds used for integrated circuit packages. The characteristics of each of the molding compounds depends on the viscosity of the resin used and the amount of silica used in the formulation. After the integrated circuits have been encapsulated they usually are tested for de-laminations at the internal interfaces, voids in the molding compound, shifts in electrical parameters, broken bond wires, cracks, and so forth.

Conventional testing of integrated circuit packages is performed by either X-ray radiography or destructive cross-sectioning, but the acoustic microscope has been used as well. There are essentially three intrinsically different types of acoustic microscopes. The first is a scanning laser acoustic microscope which introduces a continuous plane wave of ultrasound on one side of the integrated circuit package with a piezoelectric transducer and detects the transmitted ultrasound on the opposite side with a rapidly scanning laser beam. The other two acoustic microscopes are reflection mode instruments known as scanning acoustic microscopes and C-mode scanning acoustic microscopes. Each of these acoustic microscopes uses a pulse-echo transducer that is focused at or below one of the surfaces of the integrated circuit package. The transducer is scanned across the integrated circuit package in raster fashion to create an image. Typically, the scanning acoustic microscope is used for high resolution images of the surface and near surface (typically less than 25 microns (0.001 inches) deep) of the integrated circuit package. The C-mode scanning acoustic microscope can penetrate into the integrated circuit package and is ideal for probing a specific level within the package. The acoustic microscope produces a color-mapped image of the integrated circuit package based on the density of the package, the lower the amount of reflected sound, the lower the density of the package and thus greater the amount of delamination.

Conventionally, acoustic microscopy is a tool that permits integrated circuit packages to be nondestructively analyzed for the occurrence of package voids, cracking and delamination. An acoustic microscope can detect changes in density that would indicate that a package defect such as delamination occurred at a certain portion of the object under analysis. The extent of delamination can be determined by interpreting color maps generated by data processed from sound waves reflected off the device under analysis.

SUMMARY OF THE INVENTION

The present invention, generally speaking, provides a method for non-destructively identifying a type of molding compound using an acoustic microscope for identifying the molding compound used in a integrated circuit package. Although acoustic microscopes have been used for nondestructive testing for defects in integrated circuit packages, until now it has not been known to use acoustic microscopes to identify the molding compound used in integrated circuit packages. According to the present invention, an acoustic microscope is used to record different attributes of the molding compound. Each of those attributes are compared to known values for standard molding compounds to determine the molding compound.

This invention was developed as an efficient method of ascertaining whether purchased materials met requisite specifications that required specific molding compounds. At times, a molding compound may be used that is different than called for in a manufacturing specification. Prior to the present invention, a significant amount of time was necessary to verify whether the correct molding compound was utilized. When the wrong molding compound was used, additional testing was required to determine whether the substituted molding compound provided comparable results as the molding compound set forth in the specification.

In one aspect of the present invention, there is provided a method for identifying molding compound comprising providing molding compound, scanning the molding compound with an acoustic microscope, recording a plurality of attributes of the molding compound detected with the acoustic microscope, and comparing the plurality of attributes of the molding compound with known attributes of standard molding compounds to identify the molding compound provided.

In another aspect of the invention, there is provided a method for identifying molding compound in an integrated circuit package, the method comprising the steps of placing the integrated circuit package adjacent a transducer of an acoustic microscope, scanning the integrated circuit package with the transducer, recording a plurality of attributes of the molding compound in the integrated circuit package detected with the acoustic microscope, and comparing the plurality of attributes of the molding compound with known attributes of standard molding compounds to identify the molding compound of the integrated circuit package.

BRIEF DESCRIPTION OF THE DRAWING

The present invention can be further understood with reference to the following description in conjunction with the appended drawing. In the drawing.

DETAILED DESCRIPTION OF THE PREFERRED EMBODIMENTS

Figure 1:
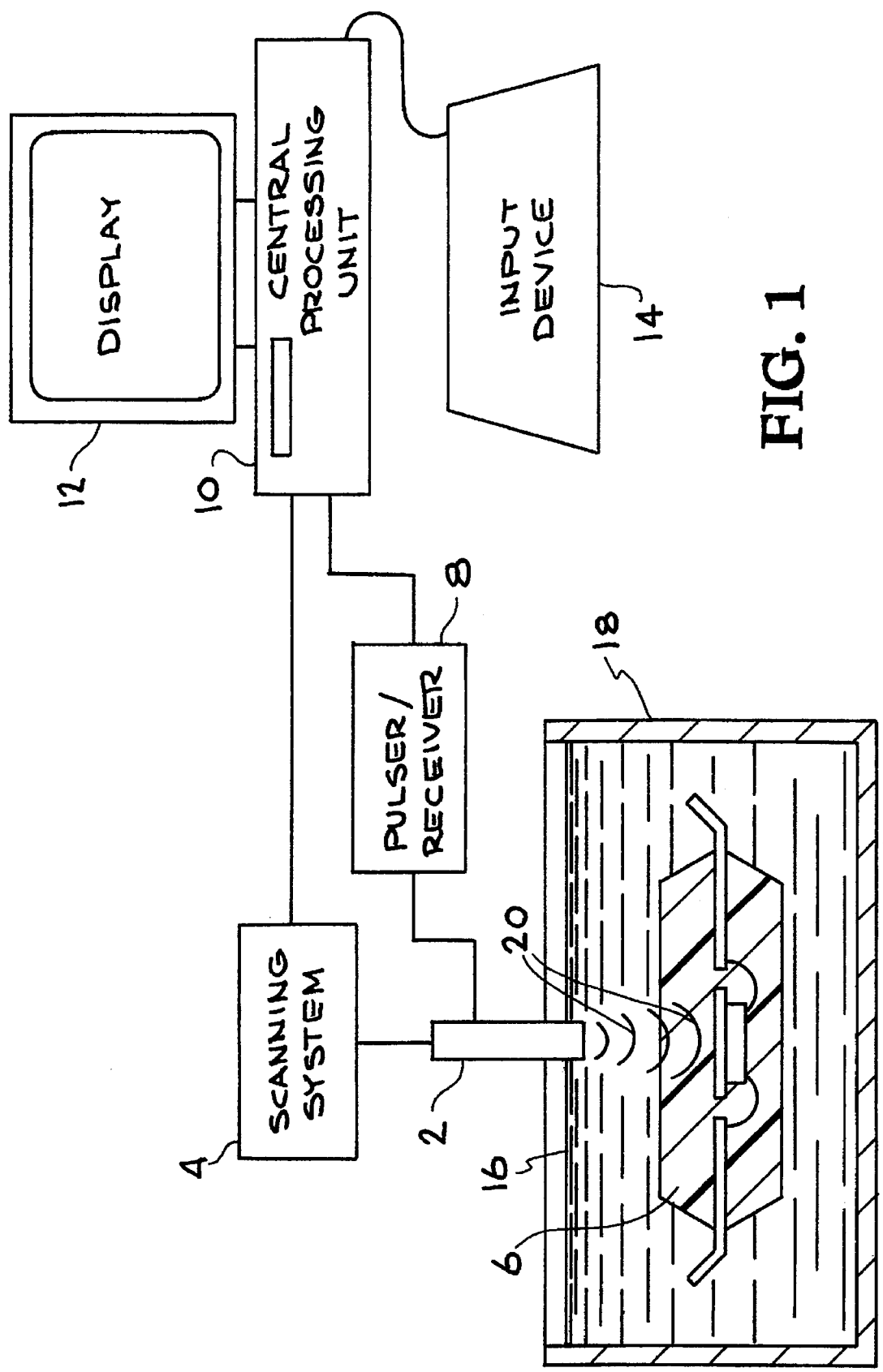
FIG. 1 is diagrammatic representation of one embodiment of a system for performing the method of the present invention.

In FIG. 1, the acoustic microscope system comprises a transducer 2 attached to a scanning system 4 connected to a computer system which can be used to move the transducer with respect to the integrated circuit package or sample 6. Transducer 2 is connected to pulser/receiver 8 which in turn is connected to a computer system comprising a central processing unit 10, display 12 and input device 14. A typical system is the "L/HF-200" provided by Sonix located at 8700 Morrisette Drive, Springfield, Va. 22152.

As to the embodiment in FIG. 1, it should be understood that the scanning system 4 is optional. The system can employ a stationary transducer and a stationary integrated circuit package. Alternatively, the transducer can be stationary and the integrated circuit package 6 moved relative to the transducer.

The acoustic microscope utilizes pulser/receiver 8 and transducer 2 to transmit focused burst of sound waves into a sample 6. Lower frequency transducers (e.g., 15 Mhz) are used for thicker samples (e.g.,2.0 mm or greater) because lower frequencies (higher energy) penetrate better. Likewise, higher frequency transducers (e.g., 25 Mhz) are used on thinner samples (e.g., 1.5 mm or less). The sample can be any of a variety of objects such as but not limited to an integrated circuit package, a sample of molding compound, or other objects containing molding compound.

In operation of the system of FIG. 1, sound waves are reflected from the sample and collected by the transducer 2. The reflected waves are sent to the receiver. The transducer 2 and sample 6 are immersed in a fluid coupling medium 16 in container 18 to acoustically couple the transducer 2 to the sample 6 because ultrasound will not travel through air. Water or an inert fluid usually is used for safety reasons. In one embodiment, the acoustic microscope transducer 2 is capable of x, y, and z-direction movement because of the scanning system 4. The z-axis is used to focus the ultrasonic sound pulse at particular depths within a sample 6 while the x and y axis permit acquisition at various locations in the plane of focus, analogous to using a high powered optical microscope.

Conventional commercial acoustic microscopes are capable of imaging in three modes: A, B, and C. In A-mode acquisition, the transducer 2 remains stationary at a single point above the sample 6 and is focused to a specific depth within the sample. A-mode operation supplies information at a single point at a specific depth. In B-mode acquisition, the transducer 2 is mechanically raster scanned in the x direction and incremented in the z direction by scanning system 4. B-mode scanning generates a cross-sectional image of a sample 6. In C-mode acquisition, the transducer 2 is mechanically raster scanned in the x-direction and incremented in the y-direction by scanning system 4. C-mode scanning generates a x-y planar image at a specific depth within the package. Any of these modes can be used to practice the system of FIG. 1.

To obtain a C-mode scan, for example, the sample 6 is placed below the transducer 2 in fluid coupling medium 16 and the acoustic wave is focused at the desired depth in the sample 6 to identify the type of molding compound in the sample. While the transducer 2 mechanically raster scans the sample 6, the transducer 2 operates alternately to transmit a sound burst 20 and receive the reflected waves. For a typical scan, as many as 64,000 sound bursts are transmitted and collected. The sound waves from each burst will be reflected at the sample surface and each subsequent interface within the sample where two adjoining materials differ in acoustic impedance. Acoustic impedance is defined as the product of the density and velocity of sound and is unique for a specific material. Values for acoustic impedance of several materials in integrated circuit packages are listed in Table 1. The reflected waves are collected by the transducer 2, processed by the receiver 8 and central processing unit 10, and displayed on display 12.

Acoustic Impedance for Several Materials
Found in Integrated Circuit Packages

| Material | Acoustic Impedance - Z kg/m$_2$s * 10$^6$ |
| --- | --- |
| Air | ~0.00 |
| Water | 1.48 |

-continued

Acoustic Impedance for Several Materials
Found in Integrated Circuit Packages

| Material | Acoustic Impedance - Z kg/m$_2$s * 10$^6$ |
| --- | --- |
| Molding Compound | ~6.76 |
| Silicon | 20.04 |
| Copper | 41.83 |
| Epoxy Resin | ~3.12 |

To generate an image at a specific plane within a sample, a "window of time" on the display 12 is defined to include the waveforms of interest. This window f time is called a gate. The gate opens for a predefined duration allowing only the information from a predetermined depth to be evaluated while excluding other depths. Conventional gates can be used, such as, but not limited to a gate for performing Fast Fourier Transforms (FFT), a front surface following gate for slaving all other gate positions to the first crossing of the front surface following gate, a sub-surface following gate for holding the data gate to a specific depth from the sub-surface following gate, a data gate, a void gate, a B-scan gate, etc.

In operation of the system of FIG. 1, the attributes generated by the central processing unit 10 are used to determine the particular molding compound in the sample 6. The attributes are calculated by the central processing unit 10 by methods generally known by one of ordinary skill in the art. Some attributes include but are not limited to voltage, maximum frequency (i.e., peak frequency), attenuation, average frequency (i.e., center frequency), and velocity. However, these attributes are used in the prior art to identify voids, cracks and delamination in integrated circuit packages based on detecting the changes in density between two adjoining materials. For example, if there is a void present in an integrated circuit package, there is a density change between the molding compound which has an impedance of approximately 6.76 and air which has an impedance of approximately 0.0, that change is reflected in the corresponding attributes and is color mapped and displayed to show the location of the void.

Each conventional molding compound used in integrated circuit packages has a unique density and the above-discussed attribute-identifying methods can be used to identify the molding compound being evaluated based on the particular density of that molding compound. Each type of molding compound has a unique density because the amount of silica is different than in other compounds and/or the viscosity of the resin is different. In the system of FIG. 1, the acoustic microscope attributes are used to identify the particular density of a compound being evaluated, then those attributes which represent the density are compared to known attributes of conventional types of molding compounds. The measured attributes can be compared to table of values of known attributes for known compounds in any of a variety of ways including, but not limited to, manually comparing each measured attribute value to each known value or using the computer system shown in FIG. 1 to compare the measured attribute values to known attribute values stored in the computer system. At least five variables can be correlated to the molding compound which a package is composed of. Those five variables are:

1) voltage calculated from the waveform (volts);
2) maximum frequency (i.e.,peak frequency of highest frequency of the wave) (Mhz);
(3) attenuation of the amplitude (4) average frequency (i.e., center frequency of the waveform) (Mhz); and (5) velocity of the sound wave penetrating the material being tested (meter/second).

Six different conventional molding compounds, in particular, 2184, 7710, 9300HH, 9710HR-2, 7325 and 7320, were evaluated with a 15 Mhz transducer with a focal length of 0.75 inches to determine standard values for the velocity, peak frequency (i.e., maximum frequency), center frequency (i.e., average frequency) voltage and attenuation for a molding compound thickness of 1.32 mm. One hundred twenty data samples were taken for each attribute and statistical evaluation was performed on those data samples to obtain the standard values given in Table II. For example, standard molding compound 2184 having a thickness of 1.32 mm has a velocity of 4.94 m/sec, peak frequency of 13.4 Mhz, center frequency of 13.5 Mhz, voltage of 0.387 volts and attenuation of 33 dB.

The system of FIG. 1 can be used to provide an objective test for reliably ascertaining the identity of the molding compound of a sample being tested. In one embodiment, the identity of an unknown molding compound sample being tested is determined by obtaining the values of at least the above five attributes for the sample under analysis using the acoustic microscope. Checking those attributes for a correspondence with each of the five standard values known to correlate to a specific molding compound of the same package size and/or thickness. By way of example, if the sample being evaluated is 1.32 mm thick, then the measured attributes would be compared to the standard values given in Table II. If a correlation is found between the measured attributes of the unknown sample and the standard values in Table II, then the identity of the molding compound for the sample being analyzed is determined to be the molding compound having the correlated standard values. Each of the measured attribute values of the unknown sample do not have to match exactly the known standard values. Each of the measured attribute values can be as much as 20% greater or less than the known standard value and an identification of the molding compound still be made.

Therefore, the molding compound can be identified from one attribute from the group of velocity, peak (i.e., maximum) frequency and center (i.e., average) frequency in combination with one attribute from the group of voltage and attenuation.

For samples which are integrated circuit packages, different packages characterized by having different dimensions (for example, thickness from the outside surface to the lead frame) will vary in the set of standard values that correspond to a particular type of molding compound because the distance that the sound travels through the material greatly affects the value of the attributes. Thus, package types such as, but not limited to, thin quad flat pack, plastic quad flat pack, plastic leaded chip carder, plastic dual in-line package, small outline integrated circuit, small outline J form, shrink small outline package, thin shrink small outline package, thin small outline package, plastic ball grid array and other plastic packages will each have unique sets for values of at least five attributes for each molding compound. However, the at least five standard values correlated to a specific molding compound will maintain the same set of values for a specific type of package. The depth (i.e., thickness) used for evaluating the sample must be the same depth used for determining the standard values of Table II because the distance that the sound travels through the material significantly affects the value of each of the attributes. In addition to the thickness of the material being important, the transducer should be set at the same height above the sample being evaluated as it was set above the sample molding compound used to determine the standard values.

There currently are three acoustic microscopy technologies any of which can be used in the system of FIG. 1. The scanning laser acoustic microscope (SLAM) is a through-transmission technique that illuminates (insonifies) the sample with a uniform plane wave of continuous wave ultrasound. SLAM uses a laser beam as a microphone by virtue of its ability to sense the small displacements (i.e., rippling) at the surface of the sample created by the sound waves passing through the sample from the bottom surface to the top surface. In most samples (which do not have shiny,

TABLE II

| Distance Back side (i.e., thickness) | Transducer | | Molding Compnd. | SAT Parameters | | | | | | Standard Values | | | | |
|---|---|---|---|---|---|---|---|---|---|---|---|---|---|---|
| | | | | Data Gate | | | FFT Gate | | Scan | Velo-city | Peak Freq. | Center Freq. | Volt-age | Atten. dB @ |
| | Mag. | Focal Lg. | | Length | Height | Start Pt. | Length | Start Pt. | dB | (m/sec) | (Mhz) | (Mhz) | (v) | 70% |
| 1.32 mm | 15 Mhz | 0.75 in. | 2184 | 0.6 μsec | 40% | 0.4 μsec | 0.3 μsec | 0.4 μsec | 35 | 4.94 | 13.4 | 13.5 | 0.397 | 33 |
| | | | 7710 | 0.6 μsec | 40% | 0.4 μsec | 0.3 μsec | 0.4 μsec | 35 | 4.78 | 5.18 | 5.15 | 0.201 | 26 |
| | | | 9300HH | 0 6 μsec | 40% | 0.4 μsec | 0.3 μsec | 0.4 μsec | 35 | 4.59 | 5.62 | 5.63 | 0.247 | 30 |
| | | | 9710HR-2 | 0.6 μsec | 40% | 0.4 μsec | 0.3 μsec | 0.4 μsec | 35 | 4.89 | 13.4 | 13.4 | 0.403 | 33 |
| | | | 7325 | 0.6 μsec | 40% | 0.4 μsec | 0.3 μsec | 0.4 μsec | 35 | 5.69 | 14.3 | 14.0 | 0.504 | 37 |
| | | | 7320 | 0.6 μsec | 40% | 0.4 μsec | 0.3 μsec | 0.4 μsec | 35 | 5.28 | 14.2 | 10.4 | 0.463 | 35 |

Differences between the resin in different molding compounds can be reflected in differences in at least the standard values for the velocity, peak frequency (i.e., maximum frequency) and center frequency (i.e., average frequency). Likewise, differences between the amount of silica in different molding compounds is reflected in differences in at least the standard values for voltage and attenuation.

optically reflective surfaces) a mirrored plastic block is placed in close proximity to the sample and is acoustically coupled to the sample. The laser is focused on a small spot on the mirror (which has corresponding ripples) and is reflected back to a photodetector where the signal is detected. An image is then displayed on a monitor.

The other two types are scanning acoustic microscope (SAM), and C-mode SAM, where the C-mode is somewhat analogous to the C-scan ultrasonic technique described above. Both the SAM and the C-SAM are reflection mode instruments in which a short duration pulse of ultrasound is focused to a small spot by an acoustic lens as previously described.

The foregoing has described the principles, preferred embodiments and modes of operation of the present invention. However, the invention should not be construed as being limited to the particular embodiments discussed and the above-described embodiments should be regarded as illustrative rather than restrictive, and it should be appreciated that variations may be made in those embodiments by workers skilled in the art without departing from the scope of the present invention as defined by the following claims.

What is claimed is:

1. A method for identifying a molding compound in an integrated circuit package comprising the steps of:

examining an integrated circuit package with an acoustic microscope;

determining a plurality of attributes of a molding compound in said integrated circuit package with the acoustic microscope; and comparing the plurality of attributes of the molding compound in said package with attributes of known molding compounds to identify the molding compound of said package.

2. The method of claim 1 wherein the plurality of attributes comprises voltage, peak frequency, attenuation, average frequency and velocity of reflected sound.

3. The method of claim 1 wherein the plurality of attributes comprises attenuation.

4. The method of claim 3 wherein the plurality of attributes further comprises peak frequency, average frequency or velocity of reflected sound.

5. The method of claim 1, wherein the plurality of attributes comprises voltage.

6. The method of claim 5, wherein the plurality of attributes further comprises peak frequency, average frequency or velocity of reflected sound.

7. A method for identifying molding compound in an integrated circuit package, the method comprising the steps of:

placing the integrated circuit package adjacent a transducer of an acoustic microscope;

transmitting sound waves into the integrated circuit package with the transducer;

determining a plurality of attributes of the molding compound in the integrated circuit package with the acoustic microscope; and comparing the plurality of attributes of the molding compound with attributes of known molding compounds to identify the molding compound in the integrated circuit package.

8. The method of claim 7 wherein the plurality of attributes comprises voltage, peak frequency, attenuation, average frequency and velocity of reflected sound.

9. The method of claim 7 wherein the plurality of attributes comprises attenuation.

10. The method of claim 9 wherein the plurality of attributes further comprises peak frequency, average frequency or velocity of reflected sound.

11. The method of claim 7, wherein the plurality of attributes comprises voltage.

12. The method of claim 11, wherein the plurality of attributes further comprises peak frequency, average frequency or velocity of reflected sound.

13. A method for identifying a molding comprising the steps of:

examining an integrated circuit package with an acoustic microscope;

determining a plurality of attributes of a molding compound in said integrated circuit package with the acoustic microscope; and comparing the plurality of attributes of the molding compound in said package with attributes of known molding compounds to identify the molding compound of said package; wherein said attributes include frequency and velocity of reflected sound.

14. The method of claim 13, wherein the frequency attribute comprises peak frequency or average frequency.

15. The method of claim 13, wherein the plurality of attributes further comprises:

voltage, or attenuation, or a combination thereof.

* * * * *